(12) United States Patent
Ito et al.

(10) Patent No.: US 7,785,622 B2
(45) Date of Patent: Aug. 31, 2010

(54) ADHESIVE PATCH FOR FENTANYL ADMINISTRATION

(75) Inventors: Takeshi Ito, Tsukuba (JP); Tetsuro Tateishi, Tsukuba (JP); Naruhito Higo, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 694 days.

(21) Appl. No.: 10/527,710

(22) PCT Filed: Sep. 12, 2003

(86) PCT No.: PCT/JP03/11689

§ 371 (c)(1),
(2), (4) Date: Apr. 22, 2005

(87) PCT Pub. No.: WO2004/024155

PCT Pub. Date: Mar. 25, 2004

(65) Prior Publication Data

US 2007/0009588 A1    Jan. 11, 2007

(30) Foreign Application Priority Data

Sep. 13, 2002    (JP) ............................. 2002-268392

(51) Int. Cl.
*A61K 31/445*    (2006.01)
*A61K 9/70*    (2006.01)

(52) U.S. Cl. ...................... 424/449; 514/317

(58) Field of Classification Search ................ 424/443, 424/448, 449; 602/48, 41, 52, 54
See application file for complete search history.

(56) References Cited

U.S. PATENT DOCUMENTS

| | | | | |
|---|---|---|---|---|
| 4,031,894 A * | 6/1977 | Urquhart et al. | ............ | 424/448 |
| 4,588,580 A | 5/1986 | Gale et al. | .................... | 424/21 |
| 5,750,136 A * | 5/1998 | Scholz et al. | ............... | 424/448 |
| 5,866,157 A * | 2/1999 | Higo et al. | ................. | 424/448 |
| 6,139,866 A | 10/2000 | Chono et al. | ................ | 424/443 |
| 6,495,159 B2 * | 12/2002 | Hirano et al. | ............... | 424/449 |
| 2002/0106401 A1 | 8/2002 | Hori et al. | .................... | 424/448 |
| 2003/0149383 A1 | 8/2003 | Ikeura et al. | .................. | 602/8 |
| 2004/0096491 A1 * | 5/2004 | Tateishi et al. | ............. | 424/449 |
| 2007/0009588 A1 * | 1/2007 | Ito et al. | ..................... | 424/449 |

FOREIGN PATENT DOCUMENTS

| | | |
|---|---|---|
| CA | 2 424 579 A1 * | 9/2002 |
| JP | 53-117034 | 10/1978 |
| JP | 61-37725 | 2/1986 |
| JP | 06-030980 | 2/1994 |
| JP | 09-315957 | 12/1997 |
| JP | 10-45570 | 2/1998 |
| JP | 11-152222 | 6/1999 |
| JP | 2000-044476 | 2/2000 |
| JP | 2002-80349 | 3/2002 |
| JP | 2003-137773 | 5/2003 |
| WO | WO 97/42952 A1 | 11/1997 |
| WO | WO 00/25792 A1 | 5/2000 |
| WO | WO 01/43729 A1 | 6/2001 |
| WO | WO 01/78690 A1 | 10/2001 |
| WO | WO 02/069942 A1 | 9/2002 |
| WO | WO 03/037393 A1 | 5/2003 |

OTHER PUBLICATIONS

Grond et al. Clinical Pharmacokinetics. 2000; 38 (1): 59-89.*

* cited by examiner

*Primary Examiner*—Shanon A Foley
(74) *Attorney, Agent, or Firm*—Licata & Tyrrell P.C.

(57) ABSTRACT

An adhesive patch for percutaneous fentanyl administration which is easily produced, has long-term continuity, and is excellent in adhesion and conformability to the skin. The adhesive patch comprises a backing layer and a pressure-sensitive adhesive layer formed on one side thereof, wherein the pressure-sensitive adhesive layer comprises fentanyl as an active ingredient, a pressure-sensitive adhesive base, and a tackifier resin, the pressure-sensitive adhesive base comprising polyisobutylene and a styrene/isoprene/styrene block copolymer, the proportion of the polyisobutylene in the adhesive base being, 8 to 15 wt. %, and the ratio of the concentration of the polyisobutylene to that of the styrene/isoprene/styrene block copolymer being from 2:3 to 3:2.

18 Claims, 1 Drawing Sheet

ADHESIVE PATCH FOR FENTANYL ADMINISTRATION

This application claims priority to international application Ser. No. PCT/JP03/11689, filed Sep. 12, 2003, and Japanese application Serial No. 2002-268392, filed Sep. 13, 2002, the entireties of which are hereby incorporated by reference herein.

DETAILED DESCRIPTION OF THE INVENTION

1. Technical Field

The invention relates to an adhesive patch which makes it possible to administer fentanyl not less than two days. Specifically, the invention relates to an adhesive patch for a percutaneous absorption, wherein it contains fentanyl in a pressure-sensitive adhesive base comprising a styrene/isoprene/styrene block polymer (SIS) and polyisobutylene (PIB) at a specific concentration.

2. Background Art

As conventional fentanyl adhesive patches are a fentanyl adhesive patch of reservoir-type (for example, see Patent document 1) and a fentanyl adhesive patch using ion pairs containing a drug salt and an organic acid salt, whereby mixed adhesive bases comprising SIS and PIB (for example, see Patent documents 2 and 3) are disclosed respectively.

However, the reservoir-type adhesive patch has demerits that 1) due to enclosing a drug as a solution or semisolid into a drug storage layer, a highly precise preparation step is required not to induce the volatilization and leakage of the content, and 2) due to the structure that needs a drug release controlling membrane necessary the process cannot avoid being complicated.

In addition, the ion-pair type adhesive patch has demerits that 1) due to necessity to add a large amount of an organic acid salt to form a stable ion-pair, there are many restrictions in conditions for the processes (milling, mixing, coating, drying) and therefore, the process is complicated, and 2) due to a high drug releasability or absorption, the progress of a drug depletion during a drug application is rapid, so that it is not suitable for maintaining a long-term drug efficacy exceeding one day.

Patent Document 1
JP, A, 61-37725 (page 1 to page 10)
Patent Document 2
JP, A, 10-45570 (page 1 to page 10)
Patent Document 3
JP, A, 2000-44476 (page 1 to page 8)

Consequently, the invention has an objective of providing an adhesive patch for percutqneous fentanyl administration which is easily produced, has long-term continuity in efficiency, and is excellent in adhesion and conformability to the skin.

DISCLOSURE OF THE INVENTION

As a result of extensive researches continued to solve the above objective, the inventors found out that by optimizing the proportion and the mix ratio of SIS and PIB the above objectives can be solved, and accomplished the invention.

Namely, the invention relates to an adhesive patch comprising a backing layer and a pressure-sensitive adhesive layer formed on one side thereof, wherein the pressure-sensitive adhesive layer comprises fentanyl as an active ingredient, a pressure-sensitive adhesive base, and a tackifier resin, the pressure-sensitive adhesive base comprising polyisobutylene and a styrene/isoprene/styrene block copolymer, the proportion of the polyisobutylene in the adhesive base being 8 to 15 wt. %, and a ratio of a concentration of the polyisobutylene to that of the styrene/isoprene/styrene block copolymer being from 2:3 to 3:2.

Also, the invention relates to the above adhesive patch, wherein the concentration of fentanyl is 1 to 6 wt. %.

Further, the invention relates to the above adhesive patch, wherein the polyisobutylene consists of a high molecular weight polyisobutylene and a low molecular weight polyisobutylene.

Also, the invention relates to the above adhesive patch, wherein an average molecular weight of the high molecular weight polyisobutylene is 900,000 to 2,500,000.

Further, the invention relates to the above adhesive patch, wherein an average molecular weight of the low molecular weight polyisobutylene is 30,000 to 65,000.

Also, the invention relates to the above adhesive patch, wherein the tackifier resin is an alicyclic saturated hydrocarbon resin.

Further, the invention relates to the above adhesive patch, wherein a proportion of the tackifier resin is 40 to 50 wt. %.

Furthermore, the invention relates to the above adhesive patch further comprising a percutaneous absorption enhancer in the pressure-sensitive adhesive layer.

Also, the invention relates to the above adhesive patch, wherein the percutaneous absorption enhancer is one or more selected from a group consisting of isopropyl myristate, isopropyl palmitate, sorbitan monooleate and oleyl alcohol.

Further, the invention relates to the above adhesive patch having an area of 10 to 75 cm² at the time of application.

As described above, the adhesive patch for percutaneous fentanyl administration of the invention has a pressure-sensitive adhesive base on a backing layer, wherein the pressure-sensitive adhesive base comprises a mixture of SIS and PIB in a specified concentration of the ratio of about 1:1 and further a tackfier resin. Such a constitution enables a long-term administration of fentanyl becomes possible. Namely, according to the adhesive patch of the invention the blood concentration of fentanyl can be kept not less than 1 ng/mL even 48 to 72 hours after application. (see the test results of the blood level). In addition, in the adhesive patch of the invention there is no agglutination of a pressure-sensitive adhesive agent and no remaining of an adhesive mass, and, therefore, the burden of a patient due to a long-term administration can be reduced.

Further, the adhesive patch of the invention does not require a pressure-adhesive layer with a drug release controlling membrane as in a reservoir-type adhesive patch and makes it possible to set up manufacturing processes (mixing, coating, drying) more easily, and, therefore, can easily be produced in an easier process compared with that of a conventional adhesive patch for percutaneous fentanyl administration.

MODE FOR CARRYING OUT THE INVENTION

Figure 1:
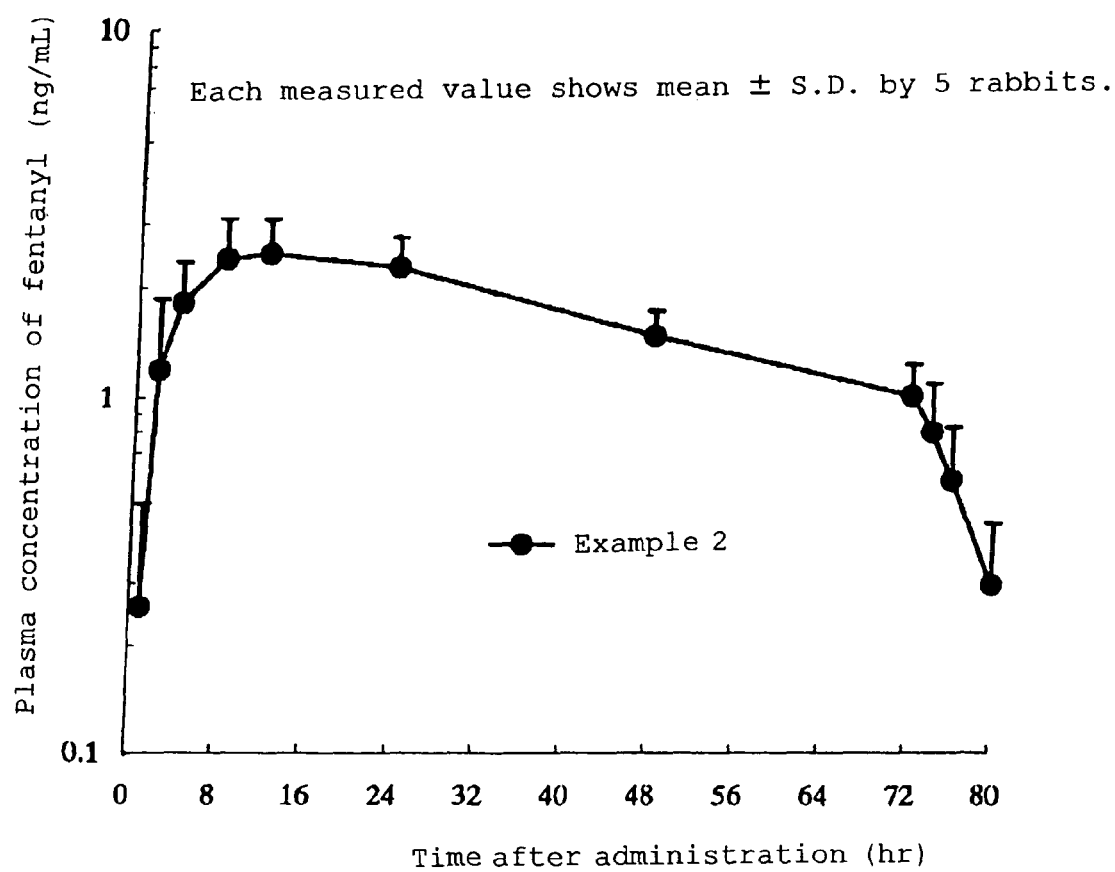
FIG. 1 shows the profile of plasma concentration of fentanyl in female rabbits after a transdermal administration of the adhesive patch of the invention (Example 2).

In the following, the adhesive patch for percutaneous fentanyl administration of the invention is further explained in detail.

A pharmacologically active substance in the adhesive patch for percutaneous fentanyl administration of the invention is fentanyl itself and does not contain a salt thereof. Said fentanyl is contained in a pressure-sensitive layer.

Further, fentanyl is blended preferably in an amount of 1 to 5 wt. % based on the total weight of the pressure-sensitive adhesive layer in the adhesive patch of the invention. By making the proportion not less than 1 wt. % it becomes easy to achieve a sufficient amount of permeation as an adhesive patch for percutaneous administration, and by making not more than 6 wt. % it is possible to surely exclude a bad effect for the physical properties of the formulation itself due to a crystalline deposition.

The fentanyl proportion of 1 to 6 wt. % is preferable because the high blood concentration can be obtained. In addition, the case in which the proportion of fentanyl is 1 to 4 wt. % is preferable in terms of physical properties of the preparation and of adhesion, and the case of 2 to 4 wt. % is particularly preferable.

In addition, the pressure-sensitive layer of the adhesive patch of the invention comprises a pressure-sensitive adhesive base and a tackifier resin.

The above pressure-sensitive adhesive base consists of PIB and SIS. The blend amount of PIB may be 8 to 15 wt. %, preferably 8 to 13 wt. %, more preferably 8 to 10 wt. %. By making the PIB blending amount not less than 8 wt. %, a sufficient adhesiveness can be obtained, and by not more than 15 wt. %, the agglutination of the pressure-sensitive adhesive base and remaining of the adhesive mass can be avoided.

PIB that contains a high molecular weight PIB and a low molecular weight PIB has a function as a pressure-sensitive adhesive agent and is preferable in terms of pressure-sensitive adhesive properties.

The average molecular weight of the high molecular weight PIB is preferably 900,000 to 2,500,000, more preferably 900,000 to 1,250,000.

In addition, the average molecular weight of the low molecular weight PIB is preferably 30,000 to 65,000, more preferably 30,000 to 53,000.

In the pressure-sensitive adhesive base SIS is mixed in addition to PIB as described above, though the ratio of the concentration thereof is 2:3 to 3:2, preferably 1:1. By mixing SIS at said proportion, the adhesive strength of an adhesive patch, which is apt for a long-term administration, the objective of the invention, can be obtained.

In addition, as a tackifier resin which is another indispensable ingredient of the pressure-sensitive adhesive layer in the adhesive patch of the invention, an alicyclic saturated hydrocarbon resin, a poly-terpene resin, petroleum resin, rosin, rosin ester and fat soluble phenol resin types are included in preferable examples. The hydrogenated petroleum is particularly preferable, and an alicyclic saturated hydrocarbon resin is further preferable. As an example of the alicyclic saturated hydrocarbon resin exemplified is Arcon P-100 (trade name; manufactured by Arakawa Kagaku Kogyo Co., Ltd.).

The concentration of the tackifier resin is preferably 40 to 50 wt. %, more preferably 42 to 50 wt. %, further preferably 44.5 to 50 wt. % based on the total weight of the pressure-sensitive adhesive layer. The concentration of the tackifier resin of not more than 50 wt. %, it becomes easy to prevent reduced adhesion to the skin due to the result that the adhesive mass becomes too hard. In addition, by making it not less than 40 wt. %, it becomes easy to obtain sufficient pressure-sensitive adhesive strength, and it becomes suitable for a long-term administration.

Further, a percutaneous absorption enhancer for fentanyl may be contained in the pressure-sensitive adhesive base of the adhesive patch of the invention. Said percutaneous absorption enhancer can be either of one or more compounds with which a percutaneous absorption promoting effect has been observed. Examples include $C_6$-$C_{20}$ fatty acids, fatty alcohols, fatty acid esters or ethers, aromatic organic acids, aromatic alcohols, aromatic fatty acid esters or ethers. Furthermore, examples include lactic acid esters, acetic acid esters, monoterpene type compounds, sesquiterpene type compounds, Azone or its derivatives, glycerol fatty acid esters, sorbitan fatty acid esters, polysorbates, polyethylene glycol fatty acid esters, polyoxyethylene hardened castor oils, sucrose fatty acid esters and the like.

Preferable examples include caprylic acid, capric acid, caproic acid, lauric acid, myristic acid, palmitic acid, stearic acid, oleicacid, linoleicacid, linolenic acid, lauryl alcohol, myristyl alcohol, oleyl alcohol, cetyl alcohol, methyl laurate, isopropyl myristate, myristyl myristate, octyldecyl myristate, cetyl palmitate, salicylic acid, methyl salicylate, glycol salicylate, cinnamic acid, methyl cinnamate, cresol, cetyl lactate, ethyl acetate, propyl acetate, isopropyl palmitate, sorbitan monooleate, geraniol, thymol, eugenol, terpineol, 1-menthol, borneol, d-limonene, isoeugenol, isoborneol, nerol, dl-camphor, glycerol monolaurate, glycerol monooleate, sorbitan monolaurate, sucrose monolaurate, polysorbate 20, polyethylene glycol monolaurate, polyethylene glycol monostearate, HCO-60 (hardened castor oil), and 1-[2-(decylthio)ethyl]azacyclopentan-2-one (hereafter abbreviated as pyrothiodecane), and in particular, fatty acid ester and aliphatic alcohol. Especially, isopropyl myristate, isopropyl palmitate, sorbitan monooleate and oleyl alcohol are preferred.

The above absorption enhancer is preferably blended in an amount of 0.01 to 20 wt. %, more preferably 0.1 to 10 wt. % and particularly preferably 0.5 to 3 wt. % based on the total weight of the pressure-sensitive adhesive layer in the preparation of the invention. By making the proportion of the absorption enhancer not more than 20 wt. %, it becomes possible to prevent skin irritations such as erythema and edema, and in not less than 0.01 wt. % a blend effect of the absorption enhancer is obtained.

Further, in the adhesive patch of the invention, a hydrophilic polymer may be blended, if required, in order to absorb aqueous constituents such as sweat from the skin. Preferable hydrophilic polymers include, for example, light anhydrous silicic acid, cellulose derivatives [carboxymethyl cellulose (CMC), carboxymethyl cellulose sodium (CMCNa), methyl cellulose (MC), hydroxypropylmethyl cellulose (HPMC), hydroxypropyl cellulose (HPC), hydroxyethyl cellulose (HEC)], starch derivatives (pullulan), polyvinyl alcohol (PVA), polyvinylpyrrolidone (PVP), vinyl acetate (VA), carboxyvinyl polymer (CVP), ethylvinyl acetate (EVA), Eudragit, gelatin, polyacrylic acid, sodium polyacrylate, polyisobutylene-maleic anhydride copolymer, alginic acid, sodium alginate, carrageenan, Arabian gum, tragacanth gum, karaya gum and polyvinyl methacrylate. In particular, light anhydrous silicic acid, cellulose derivatives (CMCNa, HPMC, HPC, MC) and Eudragit are preferred. The hydrophilic polymer is preferably blended in an amount of 0.01 to 20 wt. %, and in particular preferably 0.5 to 10 wt. % based on the total weight of the pressure-sensitive adhesive layer in the adhesive patch of the invention.

In addition, if desired, other components such as a cross-linking agent, preservative and antioxidant may be blended in the pressure-sensitive adhesive layer in the patch of the invention. Preferable cross-linking agents include, thermosetting resins such as amino resins, phenol resins, epoxy resins, alkyd resins and unsaturated polyesters, isocyanate compounds, block isocyanate compounds, organic type cross-linking agents, and inorganic type cross-linking agents such as metals or metal compounds. Preferable preservatives include ethyl p-hydroxy benzoate, propyl p-hydroxy benzoate, butyl p-hydroxy benzoate and the like. As preferable antioxidants include tocopherol and its ester derivatives, ascorbic acid, ascorbic acid-stearic acid ester, nordihydroguaretic acid, dibutyl hydroxy toluene (BHT), butyl hydroxy anisole (BHA) and the like. Further, the pressure-sensitive adhesive layer in the adhesive patch of the invention preferably consists of a nonaqueous base. By employing a nonaqueous base, the effect of the invention can be increased.

Further, in order to improve processability and adjust pressure-sensitive adhesiveness of the adhesive patch of the invention, fat as a softening agent may be blended in the pressure-sensitive adhesive layer. Preferable fat includes, for example, liquid paraffin, squalane, olive oil, camellia oil, persic oil, peanut oil and the like. In particular, liquid paraffin is preferred. Fat is preferably blended in an amount of 1 to 70 wt. %, more preferably in 10 to 60 wt. %, particularly preferably in 20 to 50 wt. % based on the total weight of the pressure-sensitive adhesive layer in the preparation of the invention.

The pressure-sensitive adhesive layer in the adhesive patch of the invention can be prepared by any conventional method. For example, in case of preparing by a solvent method, to an organic solvent solution of a blended polymer is added the other components and stirred, and then the mixture is coated on the backing layer and dried to obtain a preparation. Moreover, in a case that a blended polymer can be spread by a hot-melt method, the polymer component is dissolved at a high temperature, then added with the other components, stirred, and spread on a backing layer to obtain a preparation of the invention.

In addition, in the adhesive patch of the invention, as long as the pressure-sensitive layer is constituted by the above composition and has a backing layer to support said layer, the other layers or ingredients constituting these layers are not particularly limited, whereby the adhesive patch may be constituted by any layer. For example, the adhesive patch of the invention may contain a release liner layer set up on the pressure-sensitive adhesive layer and the like in addition to the backing layer and pressure-sensitive adhesive layer.

The above backing layer may be comprised of such as, for example, fabric, nonwoven fabric, polyurethane, polyester, polyvinyl acetate, polyvinylidene chloride, polyethylene, polyethylene terephthalate, paper, aluminum sheet and the like, or composite materials thereof.

In the adhesive patch of the invention, fentanyl is absorbed through the skin for a longer period compared with a conventional percutaneous absorption preparation, and, therefore, the invention provides a more effective method for pain relief for patients who have difficulties with oral administration of narcotic analgesic agents. In addition, the present invention enables administation with less invasion compared with a continuos subcutaneous administration method which is an invasive administration method, and, therefore, it can certainly alleviate the burden of patients.

Further, the dose can easily be adjusted by, e.g. cutting the preparation, depending on symptoms, age, body weight, sex and the like of a patient. Although the area of the adhesive patch of the invention when applyed is not particularly limited, it is preferably 10 to 60 cm$^2$, more preferably 15 to 55 cm$^2$, further preferably 20 to 50 cm$^2$. The patch being not more than 60 cm$^2$, handling thereof when applying becomes favorable, and in not less than 10 cm$^2$, a sufficient blood concentration of the effective ingredient can easily be maintained.

EXAMPLE

In the following, the invention is explained in more detail by the examples. The invention, however, is not limited to these examples, and various modification may be possible without departing from the technical spirit of the invention. Further, in the examples, '%' means wt. %' unless otherwise specified.

Example 1

| | |
|---|---|
| SIS | 8.0% |
| PIB | 8.0% |
| Arcon P-100 | 44.5% |
| Liquid paraffin | 36.7% |
| Fentanyl | 2.0% |
| Aluminum silicate | 0.8% |
| Total amount | 100.0% |

In the composition, liquid paraffin and fentanyl were stirred at room temperature, then added with toluene solution of a base and stirred, and then the mixture was coated on PET film and dried at 110° C. for 15 min. to give a pressure-sensitive adhesive layer of 50 μm, and an adhesive patch of the invention was obtained by the conventional method.

In the examples 2-4 and the comparative examples 1-4, the contents of PIB, SIS and fentanyl were as shown below and in Table 1, and the adhesive patches were prepared in the same way as that of the Example 1 except that the contents of the other ingredients were adjusted in accordance with the contents of the above ingredients.

Example 2

| | |
|---|---|
| SIS | 10.0% |
| PIB | 10.0% |
| Arcon P-100 | 46.5% |
| Liquid paraffin | 30.7% |
| Fentanyl | 2.0% |
| Aluminum silicate | 0.8% |
| Total amount | 100.0% |

Example 3

| | |
|---|---|
| SIS | 13.0% |
| PIB | 13.0% |
| Arcon P-100 | 50.0% |
| Liquid paraffin | 21.2% |
| Fentanyl | 2.0% |
| Aluminum silicate | 0.8% |
| Total amount | 100.0% |

Example 4

| | |
|---|---:|
| SIS | 10.0% |
| PIB | 10.0% |
| Arcon P-100 | 46.0% |
| Liquid paraffin | 29.2% |
| Fentanyl | 4.0% |
| Aluminum silicate | 0.8% |
| Total amount | 100.0% |

Comparative Example 1

| | |
|---|---:|
| SIS | 20.0% |
| PIB | 0.0% |
| Arcon P-100 | 46.5% |
| Liquid paraffin | 30.7% |
| Fentanyl | 2.0% |
| Aluminum silicate | 0.8% |
| Total amount | 100.0% |

Comparative Example 2

| | |
|---|---:|
| SIS | 0.0% |
| PIB | 20.0% |
| Arcon P-100 | 46.5% |
| Liquid paraffin | 30.7% |
| Fentanyl | 2.0% |
| Aluminum silicate | 0.8% |
| Total amount | 100.0% |

Comparative Example 3

| | |
|---|---:|
| SIS | 13.0% |
| PIB | 7.0% |
| Arcon P-100 | 46.5% |
| Liquid paraffin | 30.7% |
| Fentanyl | 2.0% |
| Aluminum silicate | 0.8% |
| Total amount | 100.0% |

Comparative Example 4

| | |
|---|---:|
| SIS | 7.0% |
| PIB | 13.0% |
| Arcon P-100 | 46.5% |
| Liquid paraffin | 30.7% |
| Fentanyl | 2.0% |
| Aluminum silicate | 0.8% |
| Total amount | 100.0% |

Test Example (Method)

The flux, adhesion, cohesion (agglutinative strength), adhesion to the skin (softness of preparation, placebo used) and remaining of adhesive mass to the skin (placebo used) of each preparation as described above were evaluated by the following methods. In addition, the profile of the plasma concentration of fentanyl while the adhesive patch obtained in Example 2 was applied was evaluated using rabbits.

(Skin Permeability Test)

Using each adhesive patch obtained in Examples 1-4 and Comparative examples 1-4, the following tests were carried out.

First, a back part skin of a hairless mouse was stripped, and the dermal side was placed to a receptor layer side and mounted on in a flow-through cell in which warm water of 37° C. was circulated around the outer part. Then, the adhesive patch (application area of the preparation: 5 $cm^2$) was as applied on the stratum corneum side of the skin, and samplings for the receptor solutions were carried out at every one hour for 12 hours at a rate of 10 ml/hour (hr) using the physiological saline as the receptor layer, whereby the flow amounts were measured and also the drug concentrations were measured with a high-performance liquid chromatography. The drug permeation rates per hour were calculated from the measured values to determine the drug permeation rate per unit area of the skin at a steady state. The maximum values of the drug permeation rate (maximum skin permeation rate) obtained during 24 hours from the start of the test are shown in Table 1.

(Test for Physical Properties)

With regard to each preparation in Examples 1-4 and Comparative examples 1-4, the adhesive strength was measured with a probe tack tester and a peel measuring instrument, and the agglutinative strength (cohesion) by using a creep measuring instrument respectively, and the physical properties of the preparations were evaluated by the following criteria:

o: Sufficient
×: Insufficient

The results obtained are shown in Table 1.

(Adhesion Test)

With regard to each preparation in Examples 1-4 and Comparative examples 1-4, each placebo preparation of 40 $cm^2$ was applied to the chests of 10 healthy male adults subjects for three days, and in the case that the remaining of the adhesive mass occurred when removing, the state was described. The adhesion was evaluated according to the following standards.

Then, the mean of the evaluated values of each preparation was calculated, whereby scores of not less than 3 was regarded as the sticking property o, and less than 3 was regarded as the sticking property ×.

4: No peeling
3: ¼ of the total were peeled off
2: ½ of the total were peeled off
1: ¾ of the total were peeled off (Pharmacokinetic Study in Rabbits)

The tape preparation obtained in Example 2 was cut into sheets of 14 $cm^2$, and the Pharmacokinetic Study was carried out as follows. Namely, one sheet of the above preparation was applied on each of five rabbits of Japanese White (18 week old, female, about 3 kg of body weight) whose back was shaven, and removed after 72 hours. The plasma was collected via auricle vein at 1, 2, 4, 8, 12, 24, 48, 72, 74, 76 and 80 hours after sticking of the preparation, and the fentanyl concentration in the obtained plasma was measured by LC/MS/MS. The time course behavior of the measured fentanyl concentration in the obtained plasma was shown as mean±S.D. in FIG. 1.

(Results)

As shown in Table 1, the adhesive patch of the invention was excellent in any of the adhesion, cohesion, adhesion to the skin and remaining of adhesive mass to the skin. On the contrary, the adhesion and adhesion to the skin were poor in Comparative examples 1 and 3. Comparative example 4 had defects in the cohesion and remaining of adhesive mass to the skin, and Comparative example 2 was poor also in the adhesion.

tions of fentanyl to rabbits, Jpn. Pharmacol. Ther. (Yakuri to Rinsyou), Vol. 29, No. 11, 2001, 887-897; Mizuguchi et al, Clinical evaluation of fentanyl patch (KJK-4263) toward cancer pain (1), Medicine and Drug Journal Vol. 37, No. 8, 2001/p. 2389-2402), it became clear that by the adhesive patch of the invention, fentanyl blood concentration could be kept not less than 1 ng/mL even 48 to 72 hours after application to patients.

INDUSTRIAL APPLICABILITY

According to the invention, an adhesive patch for percutaneous fentanyl administration which is easily produced, has long-term continuity, and is excellent in adhesion and conformability to the skin is provided.

The invention claimed is:

TABLE 1

| | Example 1 | Example 2 | Example 3 | Example 4 | Comparative Example 1 | Comparative Example 2 | Comparative Example 3 | Comparative Example 4 |
|---|---|---|---|---|---|---|---|---|
| SIS | 8 | 10 | 13 | 10 | 20 | 0 | 13 | 7 |
| PIB | 8 | 10 | 13 | 10 | 0 | 20 | 7 | 13 |
| Arcon (P-100) | 44.5 | 46.5 | 50.0 | 46.0 | 46.5 | 46.5 | 46.5 | 46.5 |
| Liquid paraffin | 36.7 | 30.7 | 21.2 | 29.2 | 30.7 | 30.7 | 30.7 | 30.7 |
| Fentanyl (free) | 2.0 | 2.0 | 2.0 | 4.0 | 2.0 | 2.0 | 2.0 | 2.0 |
| Aluminum silicate | 0.8 | 0.8 | 0.8 | 0.8 | 0.8 | 0.8 | 0.8 | 0.8 |
| Total | 100.0 | 100.0 | 100.0 | 100.0 | 100.0 | 100.0 | 100.0 | 100.0 |
| Flux (hairless mouse, μg/cm²/h) | 7.9 | 8.6 | 8.4 | 9.7 | 5.4 | 8.2 | 7.5 | 7.4 |
| Adhesion | ○ | ○ | ○ | ○ | ○ | X | ○ | ○ |
| Cohesion (agglutinative strength) | ○ | ○ | ○ | ○ | ○ | X | ○ | X |
| Adhesion to the skin (softness of preparation, placebo used) | ○ | ○ | ○ | ○ | X | X | X | ○ |
| Remaining of adhesive mass to the skin (placebo used) | ○ | ○ | ○ | ○ | ○ | X | ○ | X |

Meanwhile, the holding strength and remaining of adhesive mass are as described above a comparison among placebos which do not contain fentanyl. However, since fentanyl affects only lightly these physical properties, it is considered that the adhesive patch of the invention in which fentanyl is blended is excellent in the adhesion and remaining of adhesive mass.

In addition, the adhesive patch of the invention showed a sufficient value in the flux which is an indicator of the skin permeability (Table 1).

By the above results, it became clear that the adhesive patch of the invention not only gives sufficient skin permeability of fentanyl, but also is excellent in the adhesive strength, holding strength, adhesion and remaining of adhesive mass.

With the adhesive patch of the invention, the rabbit plasma concentration of fentanyl reaches to a steady state about 8 hours after sticking, the concentration of not less than 1 ng/mL being kept till 72 hours passed after sticking (FIG. 1).

Based on this result and the general information that the absobability and the time course of the plasma concentration in case of sticking a fentanyl adhesive patch to human is slower compared with those of rabbits (Otsuka et al, Parmacokinetics after subcutaneous or percutaneous administra- 1. An adhesive patch for maintaining a long-term drug efficacy of fentanyl for more than 48 hours, said patch comprising a backing layer and a pressure-sensitive adhesive layer formed on one side thereof, wherein the pressure-sensitive adhesive layer consists essentially of fentanyl as an active ingredient, a pressure-sensitive adhesive base, and a tackifier resin, wherein the pressure-sensitive adhesive base comprises polyisobutylene and a styrene/isoprene/ styrene block copolymer, the proportion of the polyisobutylene in the adhesive base being 8 to 15 wt. %, and a ratio of a concentration of the polyisobutylene to that of the styrene/isoprene/ styrene block copolymer being from 2:3 to 3:2, and wherein the tackifier resin is an alicyclic saturated petroleum resin and a proportion of the tackifier resin is from 40 to 50 wt. %, with the proviso that the adhesive patch does not contain sodium acetate.

2. The adhesive patch according to claim 1, wherein the concentration of fentanyl is 1 to 6wt. %.

3. The adhesive patch according to claim 1, wherein the polyisobutylene consists of a high molecular weight polyisobutylene and a low molecular weight polyisobutylene.

4. The adhesive patch according to claim 3, wherein an average molecular weight of the high molecular weight polyisobutylene is 900,000 to 2,500,000.

5. The adhesive patch according to claim 3, wherein an average molecular weight of the low molecular weight polyisobutylene is 30,000 to 65,000.

6. The adhesive patch according to claim 1, having an area of 10 to 75 cm$^2$ at the time of application.

7. The adhesive patch according to claim 1, wherein the alicyclic saturated petroleum resin is hydrogenated petroleum resin.

8. The adhesive patch according to claim 1, wherein the backing layer is fabric, nonwoven fabric, polyurethane, polyester, polyvinyl acetate, polyvinylidene chloride, polyethylene, polyethylene terephthalate, paper and/or aluminium sheet.

9. The adhesive patch according to claim 1 wherein the pressure-sensitive adhesive base further comprises a percutaneous absorption enhancer.

10. The adhesive patch according to claim 9, wherein the percutaneous absorption enhancer is one or more selected from a group consisting of isopropyl myristate, isopropyl palmitate, sorbitan monooleate and oleyl alcohol.

11. The adhesive patch according to claim 9, having an area of 10 to 75 cm$^2$ at the time of application.

12. The adhesive patch according to claim 9, wherein the alicyclic saturated petroleum resin is hydrogenated petroleum resin.

13. The adhesive patch according to claim 9, wherein the concentration of fentanyl is 1 to 6 wt. %.

14. The adhesive patch according to claim 9, wherein the polyisobutylene consists of a high molecular weight polyisobutylene and a low molecular weight polyisobutylene.

15. The adhesive patch according to claim 14, wherein an average molecular weight of the high molecular weight polyisobutylene is 900,000 to 2,500,000.

16. The adhesive patch according to claim 14, wherein an average molecular weight of the low molecular weight polyisobutylene is 30,000 to 65,000.

17. The adhesive patch according to claim 9, wherein the backing layer is fabric, nonwoven fabric, polyurethane, polyester, polyvinyl acetate, polyvinylidene chloride, polyethylene, polyethylene terephthalate, paper and/or aluminium sheet.

18. A method for administering fentanyl to a patient for more than 48 hours, said method comprising administering to the patient the adhesive patch of any one of claims 1-5 and 9-17.

* * * * *